United States Patent [19]

Kalchauer et al.

[11] Patent Number: 5,512,662

[45] Date of Patent: Apr. 30, 1996

[54] PROCESS FOR PREPARING METHYLCHLOROSILANES

[75] Inventors: Wilfried Kalchauer; Bernd Pachaly, both of Burghausen; Herbert Straussberger; Willi Streckel, both of Mehring, all of Germany

[73] Assignee: Wacker-Chemie GmbH, Munich, Germany

[21] Appl. No.: 384,051

[22] Filed: Feb. 6, 1995

[30] Foreign Application Priority Data

Mar. 10, 1994 [DE] Germany .......................... 44 08 113.8

[51] Int. Cl.⁶ ....................................................... C07F 7/16
[52] U.S. Cl. .................................................................. 512/472
[58] Field of Search .................................................. 512/472

[56] References Cited

U.S. PATENT DOCUMENTS

| | | |
|---|---|---|
| Re. 33,452 | 11/1990 | Ward, III et al. . |
| 2,443,902 | 6/1948 | Ferguson et al. ........................ 556/472 |
| 2,464,033 | 3/1949 | Gilliam ..................................... 556/472 |
| 2,903,473 | 9/1989 | Takami et al. ........................... 556/472 |
| 4,500,724 | 2/1985 | Ward et al. . |
| 4,504,596 | 3/1985 | Schoepe et al. . |
| 4,645,851 | 2/1987 | Prud'Homme . |
| 4,656,301 | 4/1987 | Prud'Homme et al. ................. 556/472 |
| 4,661,613 | 4/1987 | Prud'Homme . |
| 5,117,030 | 5/1992 | Cattoz et al. ........................... 556/472 |
| 5,250,716 | 10/1993 | Mui ......................................... 556/472 |
| 5,281,739 | 1/1994 | Halm et al. ............................. 556/472 |
| 5,306,328 | 4/1994 | Streckel et al. . |

FOREIGN PATENT DOCUMENTS

| | | |
|---|---|---|
| 0138679 | 4/1985 | European Pat. Off. . |
| 0440414 | 8/1991 | European Pat. Off. . |
| 0470020 | 2/1992 | European Pat. Off. . |
| 293506 | 9/1991 | Germany . |

OTHER PUBLICATIONS

D. I. Lainer et al., Chemical Abstracts 57, 6669g, 1962, "Activation of Silicon–Copper Catalysts with Antimony".

H. Lieske et al., Xth Intern. Symposium on Organosilicon Chemistry 1993, Poznań, Poland; Abstract p. 209, "Investigation of Promotor Actions with Rochow Synthesis of Methylchlorosilanes".

*Primary Examiner*—Paul F. Shaver
*Attorney, Agent, or Firm*—Martin Connaughton

[57] ABSTRACT

Methylchlorosilanes are prepared by reaction of methyl chloride with silicon in the presence of a catalyst combination of copper oxide, zinc oxide and metallic antimony.

4 Claims, No Drawings

PROCESS FOR PREPARING METHYLCHLOROSILANES

FIELD OF INVENTION

The present invention relates to a process for preparing methylchlorosilanes by reaction of methyl chloride with silicon in the presence of a catalyst combination of copper oxide, zinc oxide and metallic antimony.

BACKGROUND OF INVENTION

Processes for preparing methylchlorosilanes by reaction of silicon with methyl chloride (direct synthesis) in the presence of suitable catalysts and catalyst combinations are already known. For example, U.S. Pat. RE No. 33,452 describes a direct synthesis process using a catalyst combination of the elements or the compounds of copper, zinc and tin. The ratio of the catalysts copper, zinc and tin to one another in the process has a strong influence on the process, in particular on the productivity and the selectivity, while the form, such as metal, alloys or compounds, in which the catalysts are introduced into the catalyst composition is of subsidiary importance. Furthermore, relatively low production rates are achieved using tin as catalyst.

D. I. Lainer et al., Chemical Abstracts 57, 6669g 1962, describe a direct synthesis process in which a silicon-copper alloy containing zinc and antimony as catalysts is used. If copper is not already alloyed in the preparation of the silicon, the preparation of silicon-copper alloys is energy intensive and requires additional plants. Since the ratio silicon: copper is predetermined by these alloys, the silane synthesis is more difficult to control. Changes in the Si:Cu ratio in the catalyst composition during the reaction cannot be quickly compensated for. Use of metallic copper gives, in comparison with copper oxides, lower silane production rates (silane per mass of silicon and unit time). However, silicon-copper oxide alloys are unstable and cannot be prepared because of the electrochemical series.

Besides copper-silicon alloys, copper is usually used in the form of metallic copper, copper chloride, copper formate or copper oxalate. The preparation of these copper compounds in relatively pure form and suitable particle sizes is energy and cost intensive. Recycling of used copper for reuse in the starting compound is relatively expensive. Copper formate and oxalate are thermally labile, i.e., they can decompose spontaneously on heating. Use of copper chloride results, because of the decomposition of methyl chloride, in increased tar and soot formation on the catalyst composition and thereby in a reduction in reactivity. Metallic copper has the disadvantage that it is ductile and therefore can be mechanically comminuted only with difficulty to give a powder having a suitable particle size and surface area. A further disadvantage of metallic copper catalysts is a lower selectivity in respect of dimethyldichlorosilane. For example, the use of copper oxalate in the direct synthesis together with elemental zinc and antimony is described in DD-A-293 506.

Lieske et al., Xth Intern. Symposium on Organosilicon Chemistry 1993, Poznan, Poland; Abstract page 209 describes a direct synthesis process in which a combination of copper oxide with zinc and antimony is used as catalyst. In the preparation of the catalyst composition, metallic zinc can spontaneously undergo an exothermic redox reaction with the added copper compounds, such as copper oxides, which endangers process safety. In the reaction of the catalyst composition with methyl chloride, metallic zinc is oxidized to $ZnCl_2$. $ZnCl_2$ is partly volatile at the temperatures at which the methylchlorosilane synthesis proceeds. $ZnCl_2$ is therefore removed from the catalyst composition during the reaction and deposits on cold parts of the plant or is carried away with the silane stream. Likewise, if metallic zinc or $ZnCl_2$ is used, the catalyst composition is greatly depleted in this component during the reaction with methyl chloride. To maintain the productivity of the process, it is necessary to meter in further amounts of this component; at the same time there results an enrichment of undesired amounts of zinc compounds in the silane, on parts of the plant and in reaction dusts.

U.S. Pat. No. 4,645,851 and U.S. Pat. No. 4,661,613 propose direct synthesis processes in the presence of a catalyst combination of copper oxide, zinc oxide, metallic antimony and an addition of a further alkali metal or alkaline earth metal or metal compound, such as cesium chloride, calcium chloride or barium carbonate, but the processes were only carried out using a catalyst combination of copper oxide, zinc oxide, metallic tin and an additive. The disadvantage of such additives is that they usually have to be used in relatively high concentrations to produce corresponding effects, that most of the additives are relatively expensive and after the reaction accordingly have to be recovered or landfilled. For example, to achieve a high dimethyldichlorosilane selectivity and to increase the productivity, a high cesium chloride content is required.

SUMMARY OF INVENTION

It is an object of the present invention to provide a process for preparing methylchlorosilanes by reaction of methyl chloride with silicon, seeking a relatively high production rate and a relatively high selectivity in respect of dimethyldichlorosilane in this process, without creating, by means of further additives, problems such as a cost increase in the process or disposal of recycling of the additives after the reaction is complete.

The present invention provides a process for preparing methylchlorosilanes by reaction of methyl chloride with silicon in the presence of a catalyst combination of copper oxide, zinc oxide and metallic antimony.

By means of the process of the invention, it is possible to achieve higher silane production rates without an additional metering in of further elements or compounds being required, while simultaneously maintaining a relatively high dimethyldichlorosilane selectively. A further advantage of the invention is that the reaction mixture of silicon and catalysts described as the catalyst composition can also be safely handled at relatively high temperatures, and that the catalysts remain in sufficient concentration in the catalyst composition during the reaction.

The present invention is based on the recognition that in the system silicon/copper/zinc/antimony, the form in which the individual components are used also has a great influence on the process. Thus, for example, use of ZnO allows higher production rates to be achieved than using Zn and $ZnCl_2$; serious removal of zinc from the catalyst composition is avoided.

The process is preferably carried out in a fluidized-bed reactor, preferably in the temperature range from 250° to 400° C., in particular at from 250° to 360° C. Since it requires the least expense, the process is usually carried out at from the pressure of the surrounding atmosphere (i.e., at about 0.1 MPa) to 0.5 MPa; however it is also possible to use higher pressures.

The process can be carried out using pure methyl chloride or methyl chloride/inert gas mixtures; the inert gas used can be nitrogen or argon. In the preferred embodiment, the gas flow is selected in such a way that a fluidized bed is formed in the reactor.

The process can be carried out continuously or batchwise. Continuously means that the amounts of reacted silicon and catalysts carried out with the reaction dust are continuously replaced.

In a preferred embodiment of the process of the invention, methyl chloride or methyl chloride/inert gas mixtures are passed continuously through the catalyst composition, by which means a fluidized bed is built up. Unreacted methyl chloride and any inert gas and the gaseous methylchlorosilanes formed leave the reactor. By means of one or more cyclones, it is possible, if desired, to separate the entrained particles from the gas stream, with large entrained particles from the catalyst composition being recirculated to the reactor. The silane is subsequently separated from residual amounts of dust and unreacted methyl chloride and fed to a distillation step. Purified, unreacted methyl chloride can be refed to the reactor.

If desired, the copper contained in the entrained particles separated out, including those from the reactor residue after the reaction is complete, can be recovered by a process described in U.S. Pat. No. 5,306,328 and can be recycled in a simple manner to the copper oxide used.

In a preferred embodiment of the process of the invention, the silicon used has a particle size of less than 700 µm and greater than 20 µm, more preferably a particle size of less than 250 µm and greater than 70 µm. The average particle size of the silicon particles is preferably in the range from 100 to 200 µm, more preferably in the range from 130 to 170 µm. The silicon used usually has a purity of > 99%.

In the process of the invention, copper is used in the form of copper oxide mixtures or in the form of copper(II) oxide. In the case of mixed oxides of the formula $CuO_x$, x has a value of from 0.6 to 1, preferably a value of at least 0.7. The copper oxides used can contain a small amount of impurities such as, iron, lead, zinc, aluminum, titanium, alkali metals or alkaline earth metals or tin. The total impurities do not exceed 3% by weight, with the total concentration of lead being at most 0.005% by weight, the total concentration of alkali metals and alkaline earth metals each being at most 0.04% by weight, the total concentration of barium and strontium being at most 0.008% by weight and the total concentration of tin being at most 0.02% by weight. The copper oxides are preferably used in a particle size of less than 25 µm, with the average particle size being in the range from 10 to 0.1 µm, preferably in the range from 7 to 1 µm, and more preferably in the range of 5 to 1 µm. The copper oxides described can be prepared, by the process described in U.S. Pat. No. 5,306,328, with the oxidation state being controlled by the drying temperature and the residence time at this temperature.

Preferably, from 0.5% to 10% by weight, in particular from 0.7 to 7% by weight, of copper oxide catalyst, based on silicon used, are employed; particular preference is given to from 1% to 5% by weight.

In the process of the invention, the zinc oxide used preferably has a particle size of less than 25 µm, with the average particle size being in the range from 15 to 0.1 µm, preferably in the range from 10 to 0.5 µm. The zinc oxide used preferably contains less than 0.005% by weight of lead and less than 0.002% by weight of tin. The total content of alkali metals and alkaline earth metals is at most 0.04% by weight and the total content of barium and strontium is at most 0.008% by weight. Zinc oxide is commercially available, for example from Fluka Feinchemikalien GmbH, Germany. The amount of zinc oxide used is preferably from 0.5% to 60% by weight, in particular from 2% to 40% by weight, of ZnO, based on copper oxide; more preference is given to using from 5% to 30% by weight of ZnO.

In the process of the invention, the metallic antimony used preferably has a particle size of less than 150 µm. In a preferred embodiment, antimony powder having a particle size of at most 45 µm is used. Antimony of this particle size is commercially available, for example from Alfa-Johnson Matthey GmbH, Germany. The amount of antimony used is preferably from 200 to 8000 ppm, in particular from 300 to 4000 ppm, based on the copper oxide used; more preference is given to using from 500 to 2500 ppm of antimony.

The preparation of the catalyst composition is carried out by simple mixing of the individual components at room temperature. A subsequent thermal treatment of the catalyst composition prior to introduction into the reactor is possible, but is not carried out in the preferred embodiment.

In the following examples, unless otherwise indicated:
(a) all amounts are by weight;
(b) all pressures are 0.10 MPa (abs.);
(c) all temperatures are 20° C.

EXAMPLES

The results in reactions of silicon with methyl chloride in the presence of suitable catalysts depend, besides on the composition of the catalyst compositions, also on the construction of the experimental plant, on the way the experiment is carried out and on the silicon used. To be able to eliminate these parameters, and to unambiguously demonstrate the advantages of the invention described, various catalyst compositions described in other literature references were reacted with methyl chloride in the experimental plant described below, using a standardized procedure. The results thus obtained are given in the comparative examples and examples.

Silicon used:
Particle size in the range of 70 to 250 µm, Mean particle diameter: 150 µm, obtainable under the name "Silgrain®" from Elkem, Norway.

Experimental plant:
Laboratory fluidized-bed reactor comprising a vertical glass tube having an internal diameter of 25 mm and a height of 500 mm fitted with wrap-around heating, gas distribution frit, distillation bridge having brine cooling and reservoir flask.

Standardized procedure:
To prepare the catalyst composition, 120 g of silicon were intimately mixed with the catalysts and charged into the reactor. The catalyst composition was heated to 340° C. under a stream of nitrogen of 40 l/h, to remove traces of oxygen and moisture from the reactor. Subsequently, 40 l/h of methyl chloride were passed through the reactor and the catalyst composition was heated to 395° C. After an induction time in the range of 20 to 40 minutes, the formation of the methylchlorosilanes commenced, whereupon the reaction temperature was reduced to 360° C. The time period from this point in time until 50 ml of methylchlorosilane had formed was described as the initial phase; a further 30 ml of methylchlorosilane were subsequently collected, with this period of time being described as the production phase.

The production rates in mg of methylchlorosilane/g of silicon x minutes were calculated according to the following formulae:

$$\text{Initial phase} = \frac{\text{mg of methylchlorosilane in the initial phase}}{\text{minutes} \times \left(120 - \frac{\text{g of methylchlorosilane}}{4.75}\right)}$$

$$\text{Production phase} = \frac{\text{mg of methylchlorosilane in the production phase}}{\text{minutes} \times \text{g of silicon in the catalyst composition at the end of the reaction}}$$

The silane composition during the production phase was analyzed by means of GC, the catalyst composition at the end of the reaction was analyzed by means of ICP.

The catalysts antimony and tin which were used had an average particle size of about 40 μm; the zinc oxide, zinc and zinc chloride used had an average particle size of 1 to 10 μm, the copper catalysts used had a mean particle size of 2 to 4 μm. All catalysts, with the exception of tin, contained less than 200 ppm of tin impurities. In all catalysts, the content of alkali and alkaline earth metals was < 0.04% by weight, the total concentration of barium and strontium was < 0.008% by weight. Antimony, tin, zinc, zinc oxide, zinc chloride, cesium chloride, antimony oxide and antimony chloride are commercially available from Alfa Johnson Matthey GmbH, Germany; the copper oxides were prepared by the process described in U.S. Pat. No. 5,306,328, metallic copper was obtained by drying under argon according to this process.

Comparative Example 1

The catalyst composition corresponding to U.S. Pat. RE No. 33452; indicates that higher production rates can be obtained using antimony as catalyst under comparable conditions (see Example 1).
Catalysts:
  Partially oxidized copper $CuO_x$ having x=0.9; 6 g,
  Zinc oxide, 1 g
  Tin 1000 ppm, based on copper oxide used
  Production rate in the initial phase: 3.03
  Production rate in the production phase: 2.87.
Composition of the catalyst composition after the reaction:
  0.85% of copper
  0.25% of zinc
  13 ppm of tin
Silane composition in the production phase:
  $Me_2SiHCl$: 0.4% by weight
  $MeSiHCl_2$: 0.8% by weight
  $Me_3SiCl$: 3.7% by weight
  $Me_2SiCl_2$: 83.4% by weight
  $MeSiCl_3$: 7.2% by weight Comparative Example 2

Catalysts:
  Copper(II) oxide: 6 g
  Zinc oxide: 1 g,
  Tin 1150 ppm, based on copper oxide used
  Production rate: in the initial phase: 2.41
  Production rate in the production phase: 2.21
Composition of the catalyst composition after the reaction:
  0.84% copper
  0.19% zinc
  7 ppm tin
Silane composition in the production phase:
  $Me_2SiHCl$: 0.6% by weight
  $MeSiHCl_2$: 1.3% by weight
  $Me_3SiCl$: 3.8% by weight
  $Me_2SiCl_2$: 81.7% by weight
  $MeSiCl_3$: 7.6% by weight Example 1

Evidence that antimony catalyzes higher production rates than tin (Comparative Example 1).
Catalysts:
  Partially oxidized copper $CuO_x$ having x=0.9; 6 g
  Zinc oxide: 1 g
  Antimony 1000 ppm, based on copper oxide used
  Production rate in the initial phase: 3.03
  Production rate in the production phase: 4.03
Composition of the catalyst composition after the reaction:
  0.77% copper
  0.20% zinc
  16 ppm antimony
Silane composition in the production phase:
  $Me_2SiHCl$: 0.4% by weight
  $MeSiHCl_2$: 0.8% by weight
  $Me_3SiCl$: 4.4% by weight
  $Me_2SiCl_2$: 81.5% by weight
  $MeSiCl_3$: 8.0% by weight Example 2

Evidence that antimony catalyzes better production rates than tin (Comparative Example 2).
Catalysts:
  Copper(II) oxide: 6 g
  Zinc oxide: 1 g
  Antimony 1000 ppm, based on copper oxide used
  Production rate in the initial phase: 3.04
  Production rate in the production phase: 4.39
Composition of the catalyst composition after the reaction:
  1.46% copper
  0.36% zinc
  14 ppm antimony
Silane composition in the production phase:
  $Me_2SiHCl$: 0.2% by weight
  $MeSiHCl_2$: 0.9% by weight
  $Me_3SiCl$: 3.6% by weight
  $Me_2SiCl_2$: 81.9% by weight
  $MeSiCl_3$: 7.5% by weight Comparative Example 3

Evidence that the use of metallic zinc gives lower production rates than zinc oxide, and that zinc in this case is removed from the catalyst composition to a greater degree (comparison with Example 1, lecture by Lieske et al.).
Catalysts:
  Partially oxidized copper $CuO_x$ having x=0.9; 6 g
  Zinc 0.8 g
  Antimony 1000 ppm, based on copper oxide used
  Production rate in the initial phase: 3.14
  Production rate in the production phase: 3.39
Composition of the catalyst composition after the reaction:
  1.08% copper
  0.07% zinc
  22 ppm antimony
Silane composition in the production phase:
  $Me_2SiHCl$: 0.3% by weight
  $MeSiHCl_2$: 0.7% by weight
  $Me_3SiCl$: 5.4% by weight
  $Me_2SiCl_2$: 80.2% by weight
  $MeSiCl_3$: 8.7% by weight Comparative Example 4

Evidence that the use of $ZnCl_2$ gives lower production rates than zinc oxide, and that in this case zinc is removed from the catalyst composition to a greater degree (comparison with Example 1).
Catalysts:
 Partially oxidized copper $CuO_x$ having x=0.9; 6 g
 Zinc chloride 1.7 g
 Antimony 1000 ppm, based on copper oxide used
 Production rate in the initial phase: 0.96. The experiment was stopped after 4 hours, the production phase was not reached after 4 hours.
Composition of the catalyst composition after stopping the reaction:
 1.74% copper
 0.09% zinc
 34 ppm antimony

Comparative Example 5

Evidence that addition of CsCl to an $Si/CuO_x/ZnO/Sn$ catalyst composition does not give higher production rates than antimony-catalyzed compositions, except that in the case of antimony all disadvantages of high CsCl doping do not occur (comparison with U.S. Pat. No. 4,661,413).
Catalysts:
 Partially oxidized copper $CuO_x$ having x=0.9; 6 g
 Zinc oxide 1 g
 Tin, 1300 ppm, based on copper oxide used
 Cesium chloride 0.85 g
 Production rate in the initial phase: 3.2
 Production rate in the production phase: 3.99
Composition of the catalyst composition after the reaction:
 2.00% copper
 0.29% zinc
 42 ppm tin
Silane composition in the production phase:
 $Me_2SiHCl$: 0.1% by weight
 $MeSiHCl_2$: 1.6% by weight
 $Me_3SiCl$: 1.2% by weight
 $Me_2SiCl_2$: 87.8% by weight
 $MeSiCl_3$: 5.9% by weight

Example 3

Catalysts:
 Partially oxidized copper $CuO_x$ having x=0.8; 6 g
 Zinc oxide 1.5 g
 Antimony 1500 ppm, based on copper oxide used
 Production rate in the initial phase: 2.90
 Production rate in the production phase: 4.23
Composition of the catalyst composition after the reaction:
 1.15% copper
 0.37% zinc
 34 ppm antimony
Silane composition in the production phase:
 $Me_2SiHCl$: 0.4% by weight
 $MeSiHCl_2$: 0.8% by weight
 $Me_3SiCl$: 4.6% by weight
 $Me_2SiCl_2$: 80.4% by weight
 $MeSiCl_3$: 8.4% by weight

Comparative Example 6

Evidence that without addition of Zn, no corresponding production rates can be achieved.
Catalysts:
 Partially oxidized copper $CuO_x$ having x=0.9; 6 g
 Antimony 1000 ppm, based on copper oxide used
 Production rate in the initial phase: 0.04
 The experiment was stopped after 4 hours, the production phase was not reached after 4 hours.
Composition of the catalyst composition after stopping the reaction:
 1.10% copper
 32 ppm antimony

Comparative Example 7, 8

Evidence that the use of metallic antimony can give higher production rates than the use of antimony compounds.
Catalysts:
 Partially oxidized copper $CuO_x$ having x=0.9; 6 g
 Zinc oxide 1 g
Comparative Example 7
 Antimony oxide 1400 ppm, based on copper oxide, calculated as antimony metal.
Comparative Example 8:
 Antimony(III) chloride 1400 ppm, based on copper oxide, calculated as antimony metal.
Production rate in the initial phase:
 Comparative Example 7: 2.64
 Comparative Example 8: 1.57
In Comparative Example 8, the production phase was not reached after a reaction time of 4 hours, the reaction was stopped after 4 hours.
Production rate in the production phase in Comparative Example 7: 3.13
Composition of the catalyst composition after the reaction:

|  | Comparative Example 7 | Comparative Example 8 |
| --- | --- | --- |
| copper | 1.16% by weight | 1.47% by weight |
| zinc | 0.21% by weight | 0.24% by weight |
| antimony | 18 ppm | 45 ppm |

Silane composition in the production phase of Comparative Example 7:
 $Me_2SiHCl$: 0.5% by weight
 $MeSiHCl_2$: 1.2% by weight
 $Me_3SiCl$: 3.2% by weight
 $Me_2SiCl_2$: 82.1% by weight
 $MeSiCl_3$: 7.1% by weight

Comparative Example 9

Evidence that the use of metallic copper gives lower production rates and lower dimethyldichlorosilane selectivities than the use of copper oxides.
Catalysts:
 Metallic copper 4.8 g
 Zinc oxide 1 g
 Antimony 1250 ppm, based on copper used
 Production rate in the initial phase: 2.43
 Production rate in the production phase: 2.00
Composition of the catalyst composition after the reaction:
 2.93% copper
 0.60% zinc
 40 ppm Antimony
Silane composition in the production phase:
 $Me_2SiHCl$: 1.1% by weight
 $MeSiHCl_2$: 3.3% by weight
 $Me_3SiCl$: 3.6% by weight
 $Me_2SiCl_2$: 75.6% by weight
 $MeSiCl_3$: 13.0% by weight

What is claimed is:
1. A process for preparing methylchlorosilanes by reacting methyl chloride with silicon in the presence of a catalyst combination consisting of copper in the form of copper oxide mixtures of the formula $CuO_x$, where x has a value of 0.6 to 1 or copper (II) oxide, zinc oxide and metallic antimony.

2. The process as claimed in claim 1, wherein the amount of copper oxide used is from 0.5% to 10% by weight, based on silicon used.

3. The process as claimed in claim 1, wherein the amount of zinc oxide used is from 0.5% to 60% by weight, based on copper oxide.

4. The process as claimed in claim 1, wherein the amount of antimony used is from 200 to 8000 ppm, based on copper oxide.

* * * * *